United States Patent [19]
Dean

[11] Patent Number: 5,794,628
[45] Date of Patent: Aug. 18, 1998

[54] THERMOPLASTIC POSITIONING SLING AND METHOD OF FABRICATION THEREOF

[76] Inventor: Richard D. Dean, 21617 W. 71st Ter., Shawnee, Kans. 66218

[21] Appl. No.: 782,597

[22] Filed: Jan. 13, 1997

Related U.S. Application Data

[63] Continuation-in-part of Ser. No. 628,449, Apr. 5, 1996.

[51] Int. Cl.$^6$ ........................................................ A61F 9/00
[52] U.S. Cl. ................................ 128/858; 602/75; 606/130
[58] Field of Search ........................... 128/845, 846, 128/870, 857, 858; 602/7, 75; 5/637, 621, 628; 606/130

[56] References Cited

U.S. PATENT DOCUMENTS

| | | |
|---|---|---|
| 3,337,883 | 10/1965 | Allison . |
| 3,763,858 | 10/1973 | Buese ................................ 602/75 |
| 3,957,262 | 5/1976 | McReynolds . |
| 4,256,112 | 3/1981 | Kopf et al. .......................... 606/130 |
| 4,400,820 | 8/1983 | O'Dell et al. ...................... 128/895 X |
| 4,616,814 | 10/1986 | Harwood-Nash et al. . |
| 4,979,519 | 12/1990 | Chavarria et al. ................. 128/857 |
| 5,081,665 | 1/1992 | Kostich ............................ 602/17 X |
| 5,207,688 | 5/1993 | Carol ................................. 606/130 |
| 5,207,716 | 5/1993 | McReynolds et al. ............... 128/870 |
| 5,334,133 | 8/1994 | Carroll ............................. 128/870 X |
| 5,370,117 | 12/1994 | McLaurin, Jr. .................. 128/845 X |
| 5,531,229 | 7/1996 | Dean . |

OTHER PUBLICATIONS

Med Tec, Inc. advertisement, MT #47 3000; Jul. 1993.
Positech, Inc. advertisement re radiolucent bite block head stabilizer.
Raycast HP advertisement re radiotherapy immobilization system from nuclear associates.

Primary Examiner—Michael A. Brown
Attorney, Agent, or Firm—Hovey,Williams, Timmons & Collins

[57] ABSTRACT

An improved composite material (10) adapted for shaping to assume a desired concavo-convex configuration is provided which includes a generally flat sheet (12) of mesh-type synthetic resin (e.g., polycaprolactone) material with a layer (14) of perforate, resiliently stretchable material secured to one face of the sheet (12) by adhesive (16). The composite (10) can be warmed and used to form a concavo-convex, body part-immobilizing sling (10a). A composite (110) is also provided having a layer (114) with imperforate marginal regions (119) overlapping corresponding edges of a synthetic resin sheet (112); the margins (119) facilitate molding of the composite (110) and allow use of cantilever support legs (130).

34 Claims, 2 Drawing Sheets

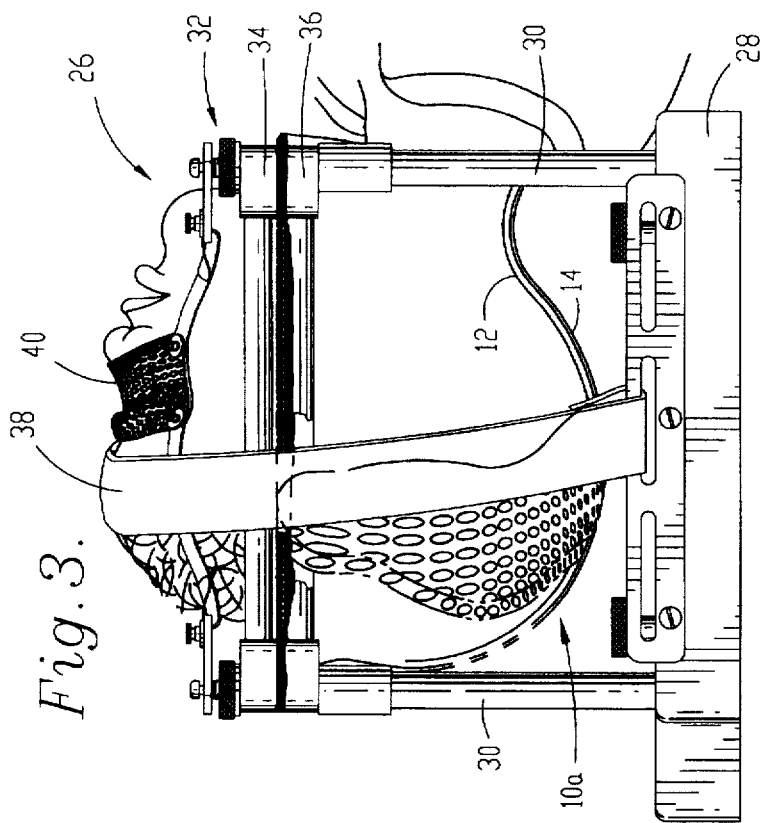
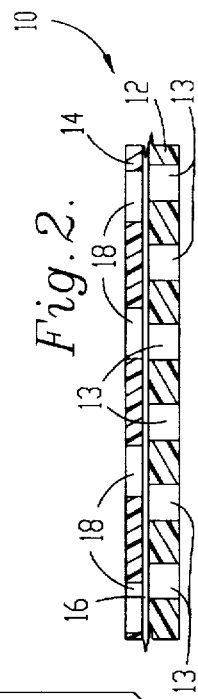
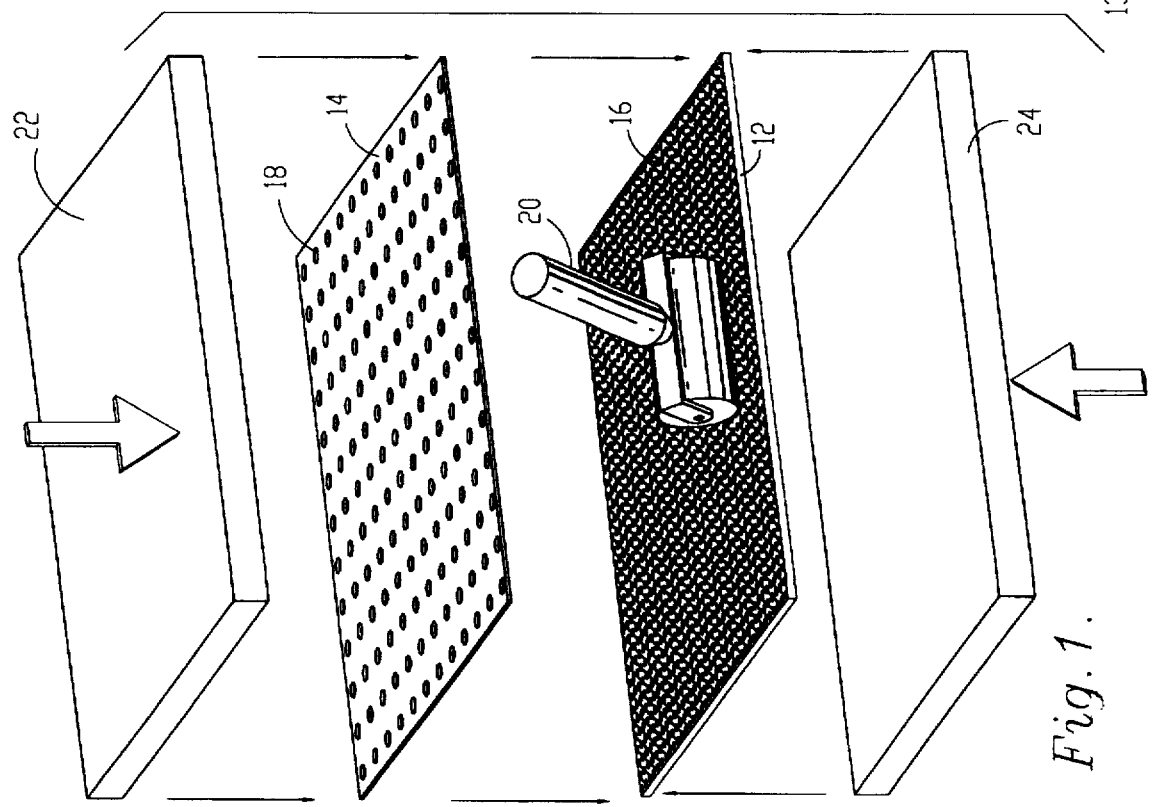

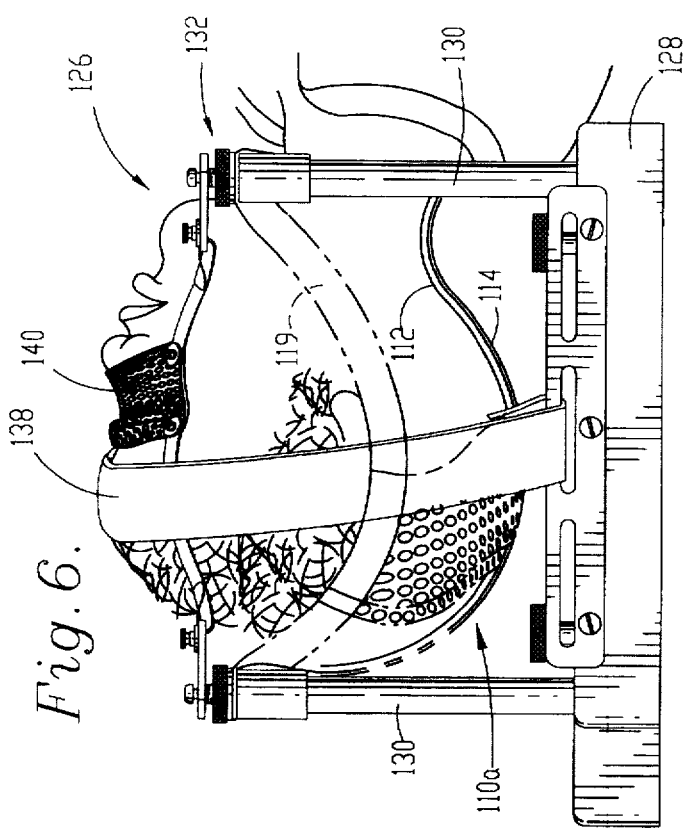
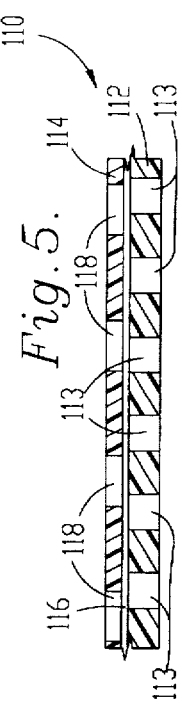
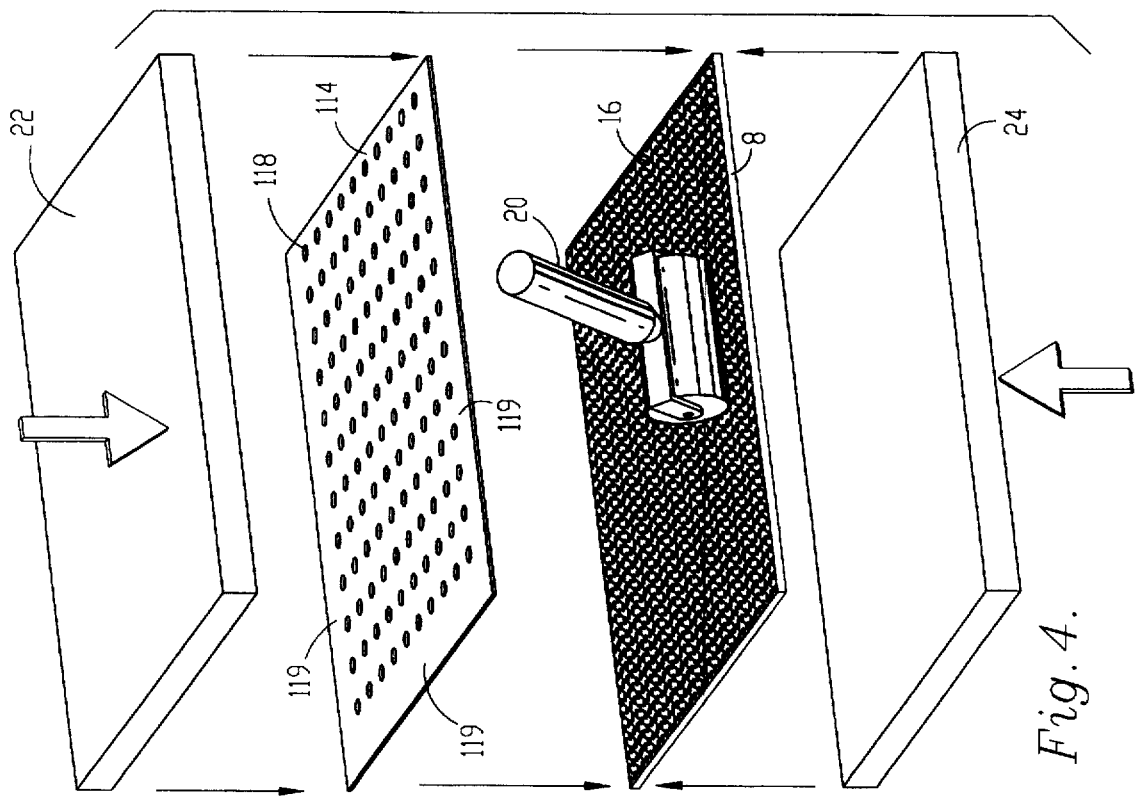
Fig.4.
Fig.5.
Fig.6.

THERMOPLASTIC POSITIONING SLING AND METHOD OF FABRICATION THEREOF

REFERENCE TO RELATED APPLICATION

This is a continuation in part of application Ser. No. 08/628,449 filed Apr. 5, 1996.

BACKGROUND OF THE INVENTION

1. Field of the Invention

The present invention is broadly concerned with an improved composite material adapted for shaping to assume a desired concavo-convex configuration, particularly in the context of forming body part-immobilizing slings used to permit more effective and repeatable medical treatments. More particularly, the invention pertains to such composite materials, methods of fabricating such composites, and body part immobilization devices, wherein the composite material is made up of a sheet of mesh-type synthetic resin material (e.g., thermoplastic polycaprolactone) with a thin layer of perforate, resiliently stretchable material such as latex rubber secured to one face of the synthetic resin sheet. In another embodiment, the margins of the latex rubber are imperforate and provide additional support for the composite; this permits suspension of the composite from corner-mounted support legs without the necessity of transverse connections between the upper ends of the support legs. It has been found that composites of this character can be more accurately prepared to conform to a selected body part, thus facilitating repeatability of placement of the body part so that successive treatments can be most effectively carried out. The composite materials of the invention greatly facilitate radiation treatments commonly prescribed for patients suffering from internal tumors.

2. Description of the Prior Art

There is frequently a need to immobilize body parts of patients undergoing medical treatment. To give but one example, patients suffering from brain tumors require repeated doses of radiation. A common problem with such patients is the need to repeatably position the patient's head in an identical location, so that radiation can be applied only to the area of the internal tumor. A related difficulty is the need for fully immobilizing the patient's head during the treatments.

A number of immobilization devices have been proposed in the past. For example, it is known to provide an essentially flat, U-shaped frame member having a stretch of perforate polycaprolactone mesh material secured therein. In initial fitting of this unit, the mesh material is warmed and stretched over the patient's face in a conforming relationship. The mesh material then quickly hardens as a shape-retaining three-dimensional pattern conforming with the patient's face. During subsequent radiation treatments, the patient is placed in a supine position on a table, and the preformed unit is placed over the patient's face in an attempt to hold the patient's head immobilized. In other alternatives, the patient may be positioned in a prone or tilted position, in accordance with the dictates of treatment and the initial fitting of the mesh material.

A problem encountered during molding of the mesh polycaprolactone material is that it tends to sag or droop when warm, thus making it difficult to accurately conform to the selected body part. This is an extremely critical issue, in that for best treatment results a ±2 mm restriction on patient motion must be maintained. Thus if the preformed mesh section or sling is inaccurate, it is difficult to maintain the degree of immobilization needed for most effective treatment.

There is accordingly a need in the art for an improved moldable material which can more accurately be formed in close, conforming relationship with a selected body part so as to give a section or sling suitable for body part immobilization.

SUMMARY OF THE INVENTION

The present invention overcomes the problems outlined above and provides a composite material adapted for shaping to assume a desired concavo-convex configuration, such as in the context of forming a body part-immobilizing section or sling. Broadly speaking, the composite material of the invention includes a generally flat sheet of mesh-type synthetic resin material characterized by the properties of being moldable upon heating thereof and becoming substantially shape retaining upon subsequent cooling. The composite further includes a thin layer of perforate, resiliently stretchable material secured to one face of the sheet, with the layer remaining secured to the sheet during molding and preferably after shaping thereof.

In preferred forms, the mesh-type sheet is formed of thermoplastic polycaprolactone material whereas the layer is adhesively secured to the sheet and formed of latex rubber material having a thickness of from about 5–20 mil. Provision of the resiliently stretchable layer affords a degree of control during the molding of the composite material in the manner of a "buoyant support." In this fashion, more accurate molding can be obtained. Preferably, though not necessarily, the layer of resilient material is maintained on the mesh-type sheet after molding of the composite and during use thereof.

In a further embodiment, the side margins of the resiliently stretchable material are imperforate, thus providing additional support for the composite and facilitating molding of the composite to a patient's head or other body part. The imperforate side margins overlap the edges of the moldable synthetic resin sheet to achieve this improvement.

BRIEF DESCRIPTION OF THE DRAWINGS

FIG. 1 is an exploded, essentially schematic view illustrating the steps followed in the fabrication of the composite materials of the invention;

FIG. 2 is an enlarged, fragmentary sectional view illustrating the construction of the composite materials of the invention;

FIG. 3 is a head immobilization device in accordance with the invention, employing a head-supporting sling formed using a composite material of the invention;

FIG. 4 is a view similar of that of FIG. 1 but illustrating the fabrication of a composite using a perforated latex sheet having solid side marginal regions;

FIG. 5 is an enlarged, fragmentary sectional view illustrating the construction of a composite fabricated using the FIG. 4 technique; and FIG. 6 is a head immobilization device in accordance with this embodiment of the invention, employing a head-supporting sling form using a composite as illustrated in FIGS. 4–5 mounted on a frame having only upstanding corner supports, with an absence of transverse frame members between the upper ends of the corner supports.

DETAILED DESCRIPTION OF THE PREFERRED EMBODIMENT

The composite material 10 of the invention (see FIG. 2) is made up of an initially flat sheet 12 of mesh-type thermoplastic polycaprolactone material, together with a layer 14 of perforate, resiliently stretchable material secured to one face of the sheet 12. Preferably, the layer 14 is affixed to sheet 12 by means of adhesive 16.

In more detail, the sheet 12 has a series of mesh openings 13 therethrough and is made up of polycaprolactone material which is readily moldable upon moderate warming, but which becomes shape-retaining thereafter. Such material is commercially available from the WAR/Aquaplast Corporation of Wyckoff, N.J. As depicted, the material is perforated ⅛" Aquaplast of orthopaedic grade. This material generally has a yield stress of about 16–17 MPa, a maximum stress of around 42–45 MPa and a percent elongation at break of from about 960–980. It will be understood, however, that while the Aquaplast material is preferred, the invention is not so limited.

The layer 14 is advantageously formed of latex rubber material, such as hygienic natural latex sheeting commercialized by The Hygienic Corporation of Akron, OH. The layer 14 should have a thickness of from about 5–20 mil, with the most preferred layer having a thickness of about 15 mil. As shown in FIG. 2, the layer 14 has a series of apertures 18 therethrough. These may be formed by any convenient means such as through the use of a manual punch; preferably, the open area presented by the apertures 18 are greater than the corresponding open areas presented by the mesh openings 13. The number and size of the apertures 18 exert a degree of control on the stretchability of the final composite 10, i.e., a greater total surface area of perforation yields a more stretchable composite, whereas a smaller total surface area gives a more rigid composite. Furthermore, the perforations allow patients to breathe when in a face-down orientation.

The adhesive 16 can be selected from a wide variety of possible materials, but the most preferred adhesive is General Electric RTV108 silicone adhesive.

Attention is next directed to FIG. 1 which schematically illustrates the method of manufacture of the composite material 10. In the first step, the mesh-type sheet 12 is provided, and a thin layer of the adhesive 16 is applied to one face of the sheet 12, using, e.g., a roller 20 or other similar expedient. Thereafter, the perforate layer is applied directly over the adhesive 16, and the composite is placed between two compression plates. A conventional clamp (not shown) is then used to compress the assembly (plates 22, 24 with the sheet 12, adhesive 16 and layer 14 sandwiched therebetween). The clamped assembly is then allowed to cure for a period of at least about 12 hours, more preferably from about 12–36 hours, and most preferably about 24 hours. This cure is preferably carried out in a humid atmosphere, such as by placing the compressed assembly in a closed container or hood adjacent to a pan of water. After the cure period, the resultant composite 10 is in the form illustrated in FIG. 2, with layer 14 adhesively secured to sheet 12.

The completed composite material 10 can be employed in the fabrication of sections or slings used with body part immobilization devices. The material 10 is particularly adapted for use in immobilization devices of the type described in U.S. Pat. No. 5,531,229, which is incorporated by reference herein. FIG. 3 illustrates a head immobilization device 26 of this variety and broadly including a generally U-shaped base 28 supporting a total of four upstanding, spaced apart, corner-mounted support legs 30. The legs 30 support a substantially U-shaped frame assembly 32 made up of corresponding upper and lower frame parts 34, 36. A preformed composite sling 10a in accordance with the invention is secured between the frame parts 34, 36 as shown. Other head immobilization aids, including strap 38 and nose bridge member 40 are also provided.

During fabrication of the device 26, a section of the initially flat composite material 10 is placed between the upper and lower frame sections 34, 36 to form a subassembly. The composite 10 is then heated by dipping the subassembly in warm water to render the composite thermoplastic. While warm, the composite is formed around the head of a patient. This is typically done with the patient in a prone or supine position with the patient's head being pressed downwardly into the warmed composite to form the desired impression. This causes the composite 10 to conform to the particular configuration of that patient's head, giving the sling 10a, which is unique for that particular patient. Upon cooling of the composite sling 10a, it maintains its shape conforming to the patient's head.

Accurate shaping of the composite material 10 is facilitated by provision of the perforate layer 14 secured to the mesh-type sheet 12. The material 14 (which as shown is normally positioned on the outside of the composite material and does not come into contact with the patient's head) gives a desirable degree of resilient or buoyant support for the sheet 12 and prevents undue sagging or drooping thereof. This insures that the sling 10a assumes the closest possible conformance with the patient's head. At the same time, the apertures 18 permit water drainage during molding and also allow air circulation during subsequent use of the sling 10a as a part of device 26.

When the patient needs radiation or other treatment, the sling 10a, mounted with the margins thereof between frame portions 34, 36, is placed on the support legs 30. The patient, lying in a recumbent position, then places his head within the preformed concavity defined by the sling 10a, as shown in FIG. 3. When this occurs, the sling 10a is placed in tension, and this serves to provide a significant degree of head immobilization. As explained in the referenced patent application, the auxiliary immobilization aids can then be attached to give an even greater degree of patient immobilization. Upon completion of the treatment, the auxiliary immobilization aids are removed and the patient is allowed to arise from the recumbent position. The subassembly defined by the frame parts 34, 36 and the captively retained sling 10a, can then be detached from the legs 30 and stored for reuse with the particular patient.

FIGS. 4–6 illustrate a second embodiment of the invention including composite material 110 made up of initially flat sheet 112 of mesh-type thermoplastic polycaprolactone material, together with a layer 114 of perforate, resiliently stretchable material secured to one face of the sheet 12. Preferably, the layer 114 is affixed to sheet 112 by adhesive 116. In the embodiment of these figures, the sheet 114 has a series of apertures 118 therethrough. In addition sheet 114 includes solid, imperforate marginal regions 119 disposed about at least three sides thereof as shown in FIG. 4. The imperforate regions 119 have a width from about 1–3 inches.

In more detail, the sheet 112 has a series of mesh openings 113 therethrough and is made up of polycaprolactone material which is readily moldable upon moderate warming, but which becomes shape-retaining thereafter. The preferred material is the same as that used for the sheet 12 of the first embodiment.

The layer 114 likewise formed of the same latex rubber material as layer 14 described above. As shown in FIG. 4, the layer 114 has a series of apertures 118 therethrough identical to apertures 18. As described above, the layer 114 also includes the imperforate marginal regions 119 formed as an integral part thereof.

The adhesive 116 can be selected from a wide variety of possible materials, but the most preferred adhesive is General Electric RTV108 silicone adhesive.

Attention is next directed to FIG. 4 of which schematically illustrates the method of manufacture of the composite material 110, which is identical to the fabrication procedure described with reference to composite 10. In the first step, the mesh-type sheet 112 is provided, and a thin layer of the adhesive 116 is applied to one face of the sheet 112, using, e.g., a roller 20 or other similar expedient. Thereafter, the perforate layer is applied directly over the adhesive 116. At this point, additional adhesive is applied to the inner face of the marginal regions 119 closest to sheet 112. These marginal regions are then folded over the adjacent edges of the sheet 112 in order to create an overlap of the latex material extending around such edges and contacting the opposite face of the sheet 112. Next, the composite is placed between two compression plates 22,24. A conventional clamp (not shown) is then used to compress the assembly (plates 22, 24 with the sheet 112, adhesive 116 and layer 114 sandwiched therebetween). The clamped assembly is then allowed to cure for a period of at least about 12 hours, more preferably from about 12-36 hours, and most preferably about 24 hours. This cure is preferably carried out in a humid atmosphere, such as by placing the compressed assembly in a closed container or hood adjacent to a pan of water. After the cure period, the resultant composite 110 is in the form illustrated in FIG. 5, with layer 114 adhesively secured to sheet 112. Moreover, although not shown in FIG. 5, the edges of the sheet 112 adjacent the regions 119 are overlapped with latex as previously described.

The completed composite material 110 can be employed in the fabrication of sections or slings used with body part immobilization devices, much in the manner of composite 10, but with important improvements. FIG. 6 illustrates a head immobilization device 126 including a generally U-shaped base 128 supporting a total of four upstanding, spaced apart, corner-mounted support legs 130. A preformed composite sling 110a in accordance with the invention is secured to the support legs 130 by means of threaded clamps 132 which are received within openings in the upper ends of the respective legs 130. It will be noted in this respect that the device 126 is free of transversely extending frame members between the upper ends of the legs 130. Other head immobilization aids, including strap 138 and nose bridge member 140 are also provided.

During fabrication of the device 126, a section of the initially flat composite material 110 is secured to the legs 130 by means of the clamps 132. The assembly is then inverted and the composite 110 is heated by dipping it in warm water. While warm and thermoplastic, the composite is formed around the head of a patient. As in the case of composite 10, this is normally done with the patient in a prone or supine position with the patient's head pressed downwardly into the warmed composite 110 to form the necessary impression. This causes the composite 110 to form to the particular patient's head giving the sling 110a unique for that one patient. Upon cooling of the sling 110a, it maintains its shape conforming to the patient's head.

It has been found that provision one of the imperforate marginal regions 119 in the layer 114 materially strengthens the edges of the composite. The edges therefore act as a "suspension bridge" when the patient's head or other body part are impressed upon it during the molding step. Furthermore, provision of the regions 119 permits suspension of the formed composite 110 without the need of upper transversely extending frame members as in the case of the first embodiment. This not only facilitates access to the sling, but also makes it easier to properly position radiation equipment adjacent the device 126.

Use of the device 126 with formed composite 110a is carried out in exactly the same manner as the previously described device 26, and the device 126 retains all of the advantages of the first-described embodiment.

Although the patient immobilization devices 26,126 have been shown as head immobilization devices, it will be appreciated that the invention is not so limited. The composite materials 10,110, with appropriate minor modifications, can be used for the immobilization of various body parts, such as the limbs or trunk region of a patient. Also, although in preferred forms, the layers 14,114 remains secured to sheets 12,112 during use of the slings 10a, 110a, it will be appreciated that the layers 14,114 could be stripped from the sheets 12,112 if desired.

Additionally, although the layer 114 has been shown with three imperforate side marginal regions 119, it would be understood that such a layer could have regions 119 extending along every side margin thereof.

I claim:

1. A composite material adapted for shaping to assume a desired concavo-convex configuration and comprising a generally flat sheet of mesh-type synthetic resin material characterized by the properties of being moldable upon heating thereof and becoming substantially shape-retaining upon subsequent cooling, and a thin layer of resiliently stretchable material having a series of apertures therethrough and secured to one face of said sheet, said layer remaining secured to said sheet during molding of said sheet, said layer presenting an inner surface adjacent said sheet and an opposed outer surface, said layer apertures being continuous and extending through the full thickness of the layer and intersecting both said inner and outer surfaces thereof, said layer being essentially solid in cross-section in the regions thereof between said apertures.

2. The composite material of claim 1, said sheet being formed of thermoplastic polycaprolactone material.

3. The composite material of claim 1, said layer being formed of latex rubber material.

4. The composite material of claim 1, said layer having a thickness of from about 5–20 mil.

5. The composite material of claim 1, including adhesive for securing said layer to said sheet.

6. The composite material of claim 1, the apertures of said layer having an area greater than the mesh openings of said sheet.

7. The composite material of claim 1, said layer remaining secured to said sheet after said shaping thereof.

8. The composite material of claim 1, said layer of material including at least one imperforate marginal region overlapping corresponding edge of said sheet.

9. The composite material of claim 8, said layer having a plurality of said imperforate marginal regions overlapping corresponding edges of said sheet.

10. The composite material of claim 1, at least certain of said apertures having a maximum cross-sectional dimension greater than the thickness of said layer.

11. A method of forming a composite material adapted for shaping to assume a desired concavo-convex configuration and comprising the steps of:

providing a generally flat sheet of mesh-type synthetic resin material characterized by the properties of being moldable upon heating thereof and becoming substantially shape-retaining upon subsequent cooling; and securing a thin layer of resiliently stretchable material having a series of apertures therethrough to one face of said sheet, said layer remaining secured to said sheet during molding of said sheet, said layer presenting an inner surface adjacent said sheet and an opposed outer surface, said layer apertures being continuous and extending through the full thickness of the layer and intersecting both said inner and outer surfaces thereof, said layer being essentially solid in cross-section in the regions thereof between said apertures.

12. The method of claim 11, said sheet being formed of thermoplastic polycaprolactone material.

13. The method material of claim 11, said layer being formed of latex rubber material.

14. The method of claim 11, said layer having a thickness of from about 5–20 mil.

15. The method of claim 11, including the step of adhesively securing said layer to said sheet.

16. The method of claim 11, the apertures of said layer having an area greater than the mesh openings of said sheet.

17. The method of claim 11, including the steps of adhesively securing said layer to said sheet, and placing said layer and sheet in compression for a period of at least about 12 hours.

18. The method of claim 17, including the step of maintaining said layer and sheet in compression in a humid atmosphere during said period.

19. The method of claim 11, including the step of securing an imperforate marginal region of said layer in overlapping relationship to a corresponding edge of said sheet.

20. The method of claim 19, including the step of securing a plurality of imperforate marginal regions of said layer in overlapping relationship to corresponding edges of said sheet.

21. The method of claim 11, at least certain of said apertures having a maximum cross-sectional dimension greater than the thickness of said layer.

22. A body part immobilization device, comprising:

a section of preformed, shape-retaining composite material presenting a concavity substantially conforming with a selected body part to be immobilized and configured for receiving and holding said selected body part, said composite material comprising a sheet of mesh-type synthetic resin material with a layer of resiliently stretchable material having a series of apertures therethrough secured to one face of said synthetic resin material, said layer presenting an inner surface adjacent said sheet and an opposed outer surface, said layer apertures being continuous and extending through the full thickness of the layer and intersecting both said inner and outer surfaces thereof, said layer being essentially solid in cross-section in the regions thereof between said apertures; and a frame assembly adapted to rest upon a support surface and operably coupled with said section for holding said concavity in an elevated position above said support surface, said frame assembly permitting placement of said body part within said concavity.

23. The device of claim 22, said synthetic resin material being polycaprolactone.

24. The device of claim 22, said frame assembly including structure for suspension of the body part within said concavity above said support surface, with said synthetic resin material being placed in tension by the weight of the suspended body part.

25. The device of claim 22, said concavity conforming with the head of a patient.

26. The device of claim 22, said layer being formed of latex rubber material.

27. The device of claim 22, said layer having a thickness of from about 5–20 mil.

28. The device of claim 22, including adhesive for securing said layer to said sheet.

29. The device of claim. 22, the apertures of said layer having an area greater than the mesh openings of said sheet.

30. The device of claim 22, said layer of material including at least one imperforate marginal region overlapping corresponding edge of said sheet.

31. The device of claim 30, said layer having a plurality of said imperforate marginal regions overlapping corresponding edges of said sheet.

32. The device of claim 22, said frame assembly comprising a plurality of upstanding support legs each adapted to support a portion of said composite material adjacent the upper end of the support leg, said frame assembly being free of connection members extending between said upper ends of said support legs.

33. The device of claim 22, at least certain of said apertures having a maximum cross-sectional dimension greater than the thickness of said layer.

34. A composite material adapted for shaping to assume a desired concavo-convex configuration and comprising a generally flat sheet of mesh-type synthetic resin material characterized by the properties of being moldable upon heating thereof and becoming substantially shape-retaining upon subsequent cooling, and a thin layer of resiliently stretchable material presenting a series of apertures therethrough and secured to one face of said sheet, said layer remaining secured to said sheet during molding of said sheet, said layer having at least one imperforate marginal region overlapping an edge of said sheet.

* * * * *